US005552307A

United States Patent [19]

Kessler et al.

[11] Patent Number: 5,552,307
[45] Date of Patent: Sep. 3, 1996

[54] METHOD OF USING AN ELICITOR TO INCREASE PRODUCTION OF METABOLITES IN BIOLOGICAL CELLS

[75] Inventors: Bezalel Kessler, Rehobot, Israel; Chaim Frenkel; Daphna Frenkel, both of North Brunswick, N.J.; Abraham Kessler, Rehobot, Israel

[73] Assignees: Bar-Ilan University, Ramat-Gan, Israel; Rutgers, The State University of New Jersey, New Brunswick, N.J.

[21] Appl. No.: 334,794

[22] Filed: Nov. 4, 1994

Related U.S. Application Data

[63] Continuation of Ser. No. 749,638, Aug. 19, 1991, abandoned, which is a continuation of Ser. No. 236,055, Aug. 24, 1988, abandoned.

[51] Int. Cl.$^6$ ................................ C12N 5/00; C12N 5/02
[52] U.S. Cl. ................................ 435/171; 435/41; 435/170; 435/240.2; 435/240.4; 435/244; 435/254.1
[58] Field of Search ................................ 47/58; 435/41, 435/172.3, 240.4, 240.46, 254.1, 256, 171, 240.1, 244, 240.2, 170

[56] References Cited

U.S. PATENT DOCUMENTS 3,628,287   12/1971   Staba ................................ 47/58

FOREIGN PATENT DOCUMENTS 3103174   of 1991   Japan ................................ 435/240.4

OTHER PUBLICATIONS

Heinstein, Peter F., Journal of Natural Products, vol. 48, No. 1, pp. 1–9, Jan.–Feb. 1985.
Marshall, Jog. et al., Phytochemistry, 1976, vol. 15, pp. 53–55.
Staba, E. John, Journal of Natural Products, vol. 48, No. 2, pp. 203–209, Mar–Apr 1985.
Chappell, Joseph et al., Plant Physiol. (1987) 85, 469–473.
Cline, Steven D. et al., Plant Physiol. (1988) 86, pp. 161–165.
Heble, M. R. et al., Planta Medica, Journal of Medicinal Plant Research, 1980 Suppl. pp. 124–128.
Abelson, Philip H., Science, vol. 247, 513 (1990).
Balandrin, Manuel F. et al., Science, vol. 228, 1154–1160 (1985).
Booth, William, Science, vol. 237, 969–970.
Staba, E. J., Chapt. 3, Applied and Fundamental Aspects of Plant Cells, Tissues and Organ Culture, Springer–verlag, Berlin, pp. 694–705 (1977).
Vlassara, Helen, Science, vol. 240, pp. 1546–1548, Jun. 10 1988.
Linsmaier and Skook, Physiol. 1965, 18:100.
Smith, et. al., Plant Cell Reports, 1987 6:142.
Kirk, et al., Enzyme Microb. Technd. 1986, 8:27.
Jaeger, et al., Appl. Environ. Microb., 1985, 50:1274.
Tien and Kirk, P.N.A.S., 1984, 81:2280.
Wood and Braun, P.N.A.S. 1961, 47:1097.
Sharma and Khanna, Ind. J. Pharm. Sci. 1981 43:175.
Murashige and Skook, Physical Planatarum, 1962 15:473.
Yeoman et al. (1980) Jn/Plant Cell Cultures; Results & Perspectives F. Sala et al. Ed. Elsevier Pub. pp. 327–343.
Vassara et al. (1985) Proc, Nat, Acad. Sci. USA vol. 82 pp. 5588–5592.
Poral etal (1985) Endocrinology vol. 116, No. 6 pp. 2293–2299.

Primary Examiner—David M. Naff
Assistant Examiner—Deborah K. Ware
Attorney, Agent, or Firm—Leroy G. Sinn

[57] ABSTRACT

A method for culturing fungal and plant cells in a culture medium containing an elicitor to increase production of a metabolite produced by the cells. For example, tobacco leaves produce the metabolite nicotine and the nicotine is produced in significantly greater amounts when the tobacco is cultured in a elicitor-containing medium. The elicitor is an oxidized Bovine Serum Albumin (BSA), or a glycosylated BSA, or an oxidized lysozyme, or glycosylated lysozyme or azetidine-2-carboxylic acid. Further, metabolite production is increased 1000% over the production of the metabolite when an elicitor is not added during the culturing method.

37 Claims, 3 Drawing Sheets

METHOD OF USING AN ELICITOR TO INCREASE PRODUCTION OF METABOLITES IN BIOLOGICAL CELLS

This application is a continuation of Ser. No. 07/749,638 filed Aug. 19, 1991 now abandoned which is a continuation of Ser. No. 07/236,055 filed Aug. 24, 1988 now abandoned.

FIELD OF THE INVENTION

The present invention relates to a method for the formation of useful metabolites in biological cells, and in particular a method for promoting or inducing the formation of such useful metabolites, by contacting the cells in culture media with elicitors.

BACKGROUND OF THE INVENTION

Plant-derived secondary metabolites form the basis of important segments of the good, pharmaceuticals, pesticide and cosmetic industries. Interest in such metabolites will continue to grow as e.g. plant sources of new and useful drugs are discovered. Moreover, it is becoming increasingly known that fungi, bacteria, algae and animal cells are also sources of potentially useful metabolic products. The recovery of useful metabolites from natural sources is in many instances constrained, however, by the remote location of such sources, and even more by the enormous quantities of source material which may be required for the isolation of utilizable quantities of the desired products, which problems are of course reflected in the often very high prices of the latter.

The problems of recovery of useful secondary metabolites from natural sources may potentially be circumvented by cell culture. Whereas in plants, for example, production of the desired products is often confined to a few specialized cells and specific differentiated tissues, as well as to limited stages in the development of the cells, under suitable cell culture incubation conditions, on the other hand, it should be possible to obtain a higher yield in the production of the metabolites, and independently of the metabolic periodicity often found in nature. In practice, however, cultured plant cells tend to lose their competence for the production of the desired metabolites, for various reasons, and to the inventors' knowledge, the only such commercial process at the present time is the production of shikonin from *Lithospermum erythrorhizon* cells in a two-stage process. Attempts to overcome such problems by cloning, selecting and subculturing, or by manipulating the culture medium, have so far not met with notable success.

If, as seems to be agreed, culture productivity is predominantly a function of the cells' own control mechanism, it should be more useful to be able to induce the synthesis of enzymes which produce useful metabolites at the gene level. It is known that enzymes may be induced by fungal elicitors after infection of plants or cultured cells by pathogens to produce phytoalexins. Elicitors are agents which induce plants to synthesize the mRNA's and enzymes required for the synthesis of the induced products (phytoalexins); extracts of mycelium or cell walls from the pathogens may serve as effective elicitors, which analysis has shown to comprise oligo- or polysaccharides and low molecular weight compounds. However, many pathogenic organisms which are sources of elicitors are relatively difficult to cultivate on a large scale. The present invention is based upon the discovery of elicitors which do not depend on the cultivation of pathogens.

These elicitors have been found to promote and induce the formation of useful metabolites in biological cells. By the term "promote" in this context, it is intended to convey that the production of useful metabolites is enhanced. However, the production of such metabolites is also induced in cell cultures which are otherwise inactive in this request.

It is accordingly an object of the present invention to provide substances which promote or induce the formation of useful metabolites in biological cells from diverse groups of organisms.

A further object of the invention is the provision of a method for the promotion or induction of the formation of useful metabolites in biological cells.

Yet a further object of the invention is the provision of such a method which utilizes elicitors.

Another object of the invention is to provide such a method by which the desired cell metabolic products may be produced in economically viable yields.

Yet another object of the invention is to provide such a method in which the elicitors are preformed.

Still another object of the invention is to provide such a method in which the elicitors are formed in situ.

A further object of the invention relates to elicitors which are novel substances.

Yet other objects of the invention will appear from the description which follows.

SUMMARY OF THE INVENTION

The present invention accordingly provides in one embodiment a method for promoting or inducing the formation of useful metabolites in biological cells, which comprises containing biological cells in a culture medium with an effective amount of at least one promoting or inducing elicitor selected from the group consisting of (1) proteins and polypeptides comprising sulfoxide moiety-containing amino acid units; (2) proteins and polypeptides comprising glycosylated amino acid units; (3) proteins and polypeptides comprising amino acid units of which at least part are sulfoxide moiety-containing and at least part are glycosylated; (4) modified proteins produced in situ by the action on biological cells of antimetabolites having the capacity to produce modified proteins; and (5) combinations thereof; the biological cells being plant cells (including calli and plant cells in suspension), fungi cells, bacteria cells, algae cells and/or animal cells.

Preferably, the method of the invention is effected in the presence of at least one of the following additional ingredients, namely:

at least one substance selected from (a) vanadium compounds and other substances effective to neutralize the effect of ATP-dependent and possible other proteases produced by the cells as a defence reaction to the presence of the at least one elicitor, and (b) particles of at least one substance selected from carborundum and other substances having sufficient hardness to abrade the surface of the cells for the purpose of improving contact between the latter and the at least one elicitor.

DETAILED DESCRIPTION OF THE INVENTION

Figure 1:
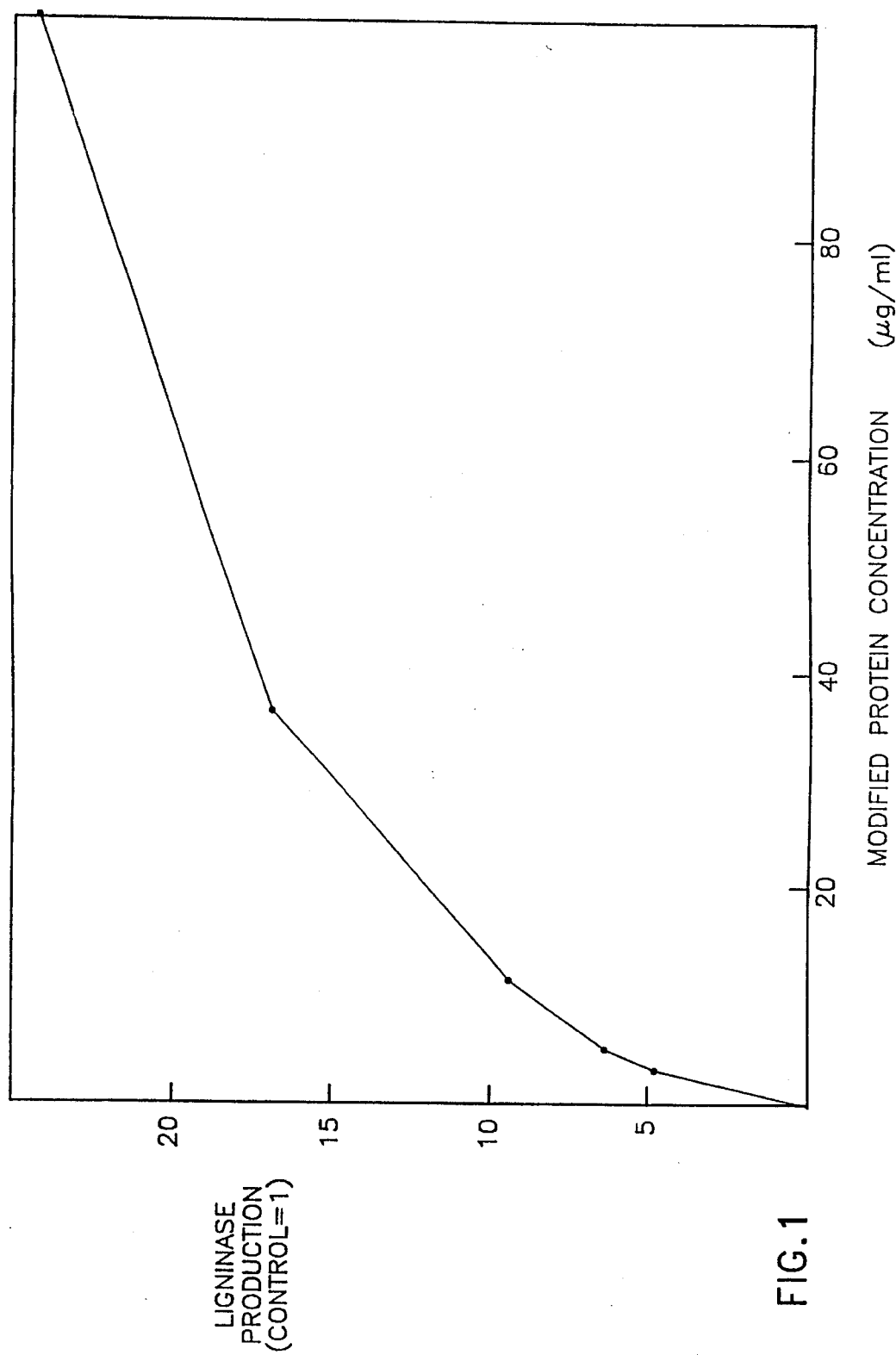
FIG. 1 shows the variation of the amount of useful metabolite produced with elicitor concentration, in accordance with an embodiment of the method of the invention.

In an embodiment of the method of the invention, the elicitor may, for example, comprise at least one member selected from naturally occurring thioether moiety-containing proteins wherein at least part of the thioether content has been replaced by sulfoxide in vitro and such proteins which have in addition been glycosylated in vitro. In another embodiment of the method of the invention there may be used glycosylated proteins which need not contain thioether or sulfoxide moieties.

In a particular embodiment of the method of the invention, the elicitor may comprise at least one sulfoxide moiety-containing protein isolated from natural sources, or a derivative thereof made by glycosylation in vitro.

In yet another embodiment of the method of the invention, the elicitor comprises at least one thioether moiety-containing polypeptide not occurring in nature or/and such polypeptide which has been glycosylated, and in which at least part of the thioether content has been replaced by sulfoxide.

In still another embodiment of the method of the invention, the elicitor comprises polymethionine in which at least part of the thioether content has been replaced by sulfoxide or/and polymethionine which has been glycosylated and in which at least part of the thioether content has been replaced by sulfoxide.

The elicitors may be introduced into the cell culture media in concentrations of up to (e.g.) about 300 μg./ml.

While the present invention is not to be restricted by any theory of action, nevertheless it is presently believed that the elicitors elicit the transcription of new mRNA's followed by the formation of enzymes which lead to the production of various cell-specific products. In some cases, abnormal proteins of promoting or inducing potential were synthesized in situ by the presence of antimetabolites having the capacity to produce modified proteins such as azetidine-2-carboxylic acid; it will be apparent to those skilled in the art that other equivalent antimetabolites having the capacity to produce modified proteins could potentially be utilized for a similar purpose.

The use of particles of added carborundum, or other abrading substance (such as e.g. tungsten carbide or boron carbide) of sufficient hardness to abrade the surface of the cells for the purpose of improving contact between the latter and the at least one elicitor, in accordance with an embodiment of the invention, has already been mentioned; it is especially useful in cultures of cells of higher plants and of algae. Also mentioned above, was the optional use of a vanadium compound, preferably of pentavalent vanadium such as a metavanadate or orthovanadate, e.g. sodium metavanadate or orthovanadate. The vanadium compound can in some cases be replaced by other nonspecific protease inhibitors such as heparin, poly (glut-tyr) (at a 1:1 ratio) and polyanions.

Examples of particular preformed elicitors (to which the invention is of course not limited) which may be utilized within the scope of the invention are:

(a) bovine serum albumin, lysozyme, collagen and hemoglobin in which at least some of the thioether moieties in the methionine residues have been replaced by sulfoxide, as e.g. by oxidation with oxidizing agents such as hydrogen peroxide;

(b) polymethionine (which is commercially available as the poly-L-form in molecular weight ranges of e.g. 5–15, 16–36, 30–50 and 100–200×$10^3$), in which the thioether moieties in the methionine residues have been replaced by sulfoxide, as e.g. by oxidation with oxidizing agents such as hydrogen peroxide;

(c) purified protein of pea and other legume seeds, which contain methionine residues of which about 20% have been oxidized (i.e. the thioether moieties are in sulfoxide form);

(d) Amadori protein products of lysozyme, protamine and hemoglobin, which have been submitted to a prolonged glycosylation process; and (e) the products specified in (a), (b) and (c), which have been subjected to glycosylation.

It is presently contemplated that the invention will be applicable to the production of (e.g.) the following classes of plant-derived alkaloids, flavanoids, glycosides, naphthoquinones, polyphenols, steroids, tannins and terpenoids, and more particularly to the products of commerce mentioned below.

Food Ingredients

Colors: anthocyanins, betacarotene, betacyanins, canthaxanthin and saffron.

Flavors: strawberry, grape, vanilla, tomato, celery, asparagus.

Oils: mint, rose, vetiver, jasmine, patchouly, sandalwood, lemon, onion, garlic.

Sweeteners: stevioside, thaumatin, miraculin, monellins.

Agricultural Chemicals

Pyrethrins, rotenone, azadirachtin, neriifolin, solanine, alleopathic chemicals.

Pharmaceuticals

Codeine, morphine, scopolamine, atropine, colchicine, cocaine, vinblastine, L-dopa, hyoscyamine, diosgenin, digitoxin, digoxin, quinidine, quinine, vincristine, shikonin, ajmalicine, serpentine, physostigmine, pilocarpine, tubocurarine, eicosapentaenoic acid.

Unclassified Pigments

Phycobiliproteins such as phycocyanins, phycoerythrins, allophycocyanine and phytochrome.

It is moreover within the ambit of the present invention to produce useful metabolites from animal cells, e.g. cytokines from blood cells.

Lignin is the most abundant organic material next to cellulose and is in any case the most abundant waste material. It is a complex polymeric material containing phenylpropanoid subunits, so that it is potentially the source of aromatic chemicals, although in practice it has so far been found resistant to biodegradation. A fungal enzyme, ligninase, has been isolated, and this can depolymerize lignin, but its exploitation has so far been limited by a number of factors including its scarcity. According to the prior art, the enzyme-carrying fungus requires a 100% oxygen atmosphere for ligninase formation. It has surprisingly been found in accordance with a particular embodiment of the present invention, that by utilizing elicitors as disclosed herein, a notable increase in ligninase yield from the fungus *Phanerochaete chrysosporium* is obtained in absence of a 100% oxygen atmosphere.

The method of the present invention as applied to the production of ligninase is believed to pen new vistas for lignin treatment. The potential availability of ligninase on a industrial scale, applied to the wood utilization industries in place of the current chemical methods should improve quality by causing less damage to cellulose fibers, reducing yellowing and cutting energy costs by perhaps 30%. It is believed that enzyme treatment could be used in existing paper plants. Isolation from lignin treatment of useful aromatic compounds such as vanillin, and other flavorings and fragrances, would also be a potential gain derived from this particular application of the method of the present invention. Ligninase is also active in the detoxification of hazardous waste material such as chlorinated lignin, polycyclic aromatic pollutants, TNT, etc.

The term "ligninase" as used herein is intended as a functional term and is not intended to imply any particular limitation as to the chemical structure thereof.

Experiments conducted by the inventors have shown the following non-limitative examples of advantageous results, when applying the process of the invention by use of S-oxidized and glycosylated proteins or polypeptides.

1. In cultured cells of *Nicotiana tabacum* (tobacco) the yield of nicotine was enhanced up to 100–1000 fold; the yield of other unidentified metabolites was also increased similarly.

2. In cultured undifferentiated *Atropa belladona* leaf cells the yield of atropine was enhanced 100–1000 fold; the yield of other unidentified metabolites was also increased similarly. This result is of particular significance since in Belladona only cultures roots produce detectable atropine levels.

3. In cultures cells of *Dioscorea deltoides* (Mexican yam) the yield of diosgenin was increased 5 to 10 times.

4. In cultured cells of *Catharanthus roseus* (rosy periwinkle) the yield of anticancer alkaloids was increased almost 100 times.

5. Modified proteins were found to stimulate the production of useful metabolites (such as those indicated in parentheses) in the microalgae *Porphyridium cruentum* and *Monodus subterraneous* (eicosapentaenoic acid, arachidonic acid); and *Haematococcus sp.* (canthaxanthin).

6. In cultures cells of white rot fungus (*Phanerochaete chrysosporium*) the yield of ligninase was increased about 20 times, in comparison with untreated cells.

The invention will now be illustrated by the following non-limitative examples.

EXAMPLE I

*Nicotiana tabacum* cv. Xanthi (tobacco) leaf cells (about 300–400 mg. fresh weight per flask) were grown in the dark in suspension in a growth medium, as described by Murashige and Skook (Physiol. Plantarum 1962 15: 473), containing 1 mg./l. 1-naphthaleneacetic acid, 0.1 mg./l. kinetin and 3% sucrose in 125 ml. Erlenmeyer flasks on a rotary shaker (120 rpm, 25° C.). The volume of growth medium per flask was 30 ml., which contained about 10–20 mg. fine mesh carborundum. Comparative runs were carried out with and without addition to the medium of modified protein in the form of oxidized BSA (20 µg./ml.). After 4 weeks, the cells were harvested, weighted, frozen and lyophilized. The dried cells were extracted with methanol in a Soxhlet extractor and the extract was evaporated to dryness at 40° C. with a Buchi Rotoevaporator. The residue was dissolved in 0.5N HCl and extracted with ether. The aqueous layer was brought to pH 9.5 with NaOH, extracted twice with ether and the combined two ether extracts were dried with $K_2CO_3$, prior to adding HCl and then evaporating to dryness. The residue was dissolved in 0.5N HCl and aliquots were applied to TLC plates of silica gel G (Merck). The plates were developed in 85:14:1 chloroform-ethanol-ammonia, dried in a stream of $N_2$, and alkaloids were visualized by Dragendorff's reagent. Quantitatively the alkaloids were determined by GLC analysis. In absence of elicitor there were obtained $2.8 \times 10^{-3}\%$ (dry weight) nicotine, compared with 2.2% (dry weight) in presence of elicitor, the latter representing a $7.8 \times 10^3$ fold enhancement of yield. The dry weight of cells at the end of the run was 3.2 g. per flask.

EXAMPLE II

*Belladona atropa* cells (about 200 mg. fresh weight per flask) were grown in suspension in a medium described by Wood and Brown (P.N.A.S. 1961 47:1907) and Sharma and Khanna (Ind. J. Pharm. Sci. 1981 43: 175), containing 0.22 mg./l. 2,4-dichlorophenoxyacetic acid and 2.0 mg./ml. kinetin. The volume of growth medium per flask was 30 ml., which contained about 10–20 mg. fine mesh carborundum. Comparative runs were carried out with and without addition to the medium of elicitor in the form of oxidized BSA (20 µg./ml.). After 5–6 weeks, the cells were harvested, weighted, frozen and lyophilized. Further processing of the harvested cells and determination of the alkaloids by TLC and GLC, was carried out as described in Example I. In absence of elicitor $1.8 \times 10^{-4}\%$ (dry weight) atropine were obtained, compared with 0.2% (dry weight) in presence of elicitor, the latter representing a $1.1 \times 10^3$ fold enhancement of yield. The dry weight of cells at the end of the run was 2.1 g. per flask.

EXAMPLE III

*Dioscorea deltoides* (Mexican yam) cells (about 300–400 mg. fresh weight per flask) were grown in the dark in suspension in a growth medium, as described by Murashige and Skook (Physiol. Plantarum 1962 15: 473), containing 0.1 mg./l. 2,4-dichlorophenoxyacetic acid, 1 mg./l. nicotinic acid, 10 mg./l. thiamine-HCl, 1 mg./l. pyridoxine-HCl and 100 mg./l. inositol, in 125 ml. Erlenmeyer flasks on a rotary shaker (100 rpm, 28° C.). The volume of growth medium per flask was 30 ml., which contained about 10–20 mg. fine mesh carborundum and about 10 mg. sodium orthovanadate. An approximately equimolar amount of sodium metavanadate could be used instead of the orthovanadate. Comparative runs were carried out with and without addition to the medium of elicitor in the form of oxidized BSA (20 µg./ml.). After about 3 weeks, the cells were harvested, lyophilized, refluxed for 2 hours in 2N HCl, filtered, washed with water and dried. The cells were then extracted with chloroform at 60° C., the extract was filtered and evaporated to dryness, and the residue was taken up in chloroform and chromatographed. The spots were visualized with antimony chloride in chloroform. The spots were then dissolved in chloroform and the O.D. read in a spectrophotometer. Some determinations were made by GLC. In absence of elicitor there were obtained 0.1% (dry weight) diosgenin, compared with 3.8% (dry weight) in presence of elicitor, the latter representing a 38 fold enhancement of yield. The dry weight of cells at the end of the run was 1.6 g. per flask.

EXAMPLE IV

*Catharanthus roseus* (rosy periwinkle) cells were grown in suspension in Linsmaier-Skook's medium (Physiol. Plantarum 1965 18: 100) containing 0.22 mg./l. 2,4-dichlorophenoxyacetic acid and 2.0 mg./ml. kinetin. The volume of growth medium per flask was 30 ml., which contained about 10–20 mg. fine mesh carborundum. Comparative runs were carried out with and without addition to the medium of elicitor in the form of oxidized BSA (20 µg./ml.). After 4 weeks, the cells were harvested, and the alkaloids were extracted as described by Smith et al (Plant Cell Rep. 1987, 6: 142) and assayed by TLC. The plates were developed by 3:1 ethyl acetate/absolute ethanol and were then viewed first under UV, afterwards spraying with ceric ammonium sulfate. Qualitative and quantitative analyses were also conducted by mass spectroscopy. In absence of modified protein there were obtained $1.2 \times 10^{-3}\%$ (dry weight) alkaloids (vinblastine+vincristine+catharantine+ajmalicine), compared with 0.1% (dry weight) in presence of elicitor, the latter representing an 83 fold enhancement of yield.

EXAMPLE V

Cells of white rot fungus (*Phanerochaete chrysosporium*) were grown in air in a chemically defined standard medium (Kirk et al, Enzyme Microb. Technol. 1986 8: 27) in absence or presence of Tween 20 (Jaeger et al, Appl. Environ. Microb. 1985 50: 1274). The volume of growth medium per flask was 30 ml.; no carborundum was used. Comparative runs were carried out with and without addition to the medium of elicitor in the form of oxidized BSA (10 µg./ml.) After 3–4 days, the cultures were filtered through Whatman No. 1 filter paper, and ligninase activity in the solution was measured by determining the rate of oxidation of veratryl alcohol to veratraldehyde (Tien and Kirk, P.N.A.S. 1984 81: 2280). by following the change in optical density at 310 nm per min., per ml. of enzyme solution. In presence of elicitor there was obtained a 20-fold increase in the optical density as compared with a control experiment not using elicitor.

Figure 2:
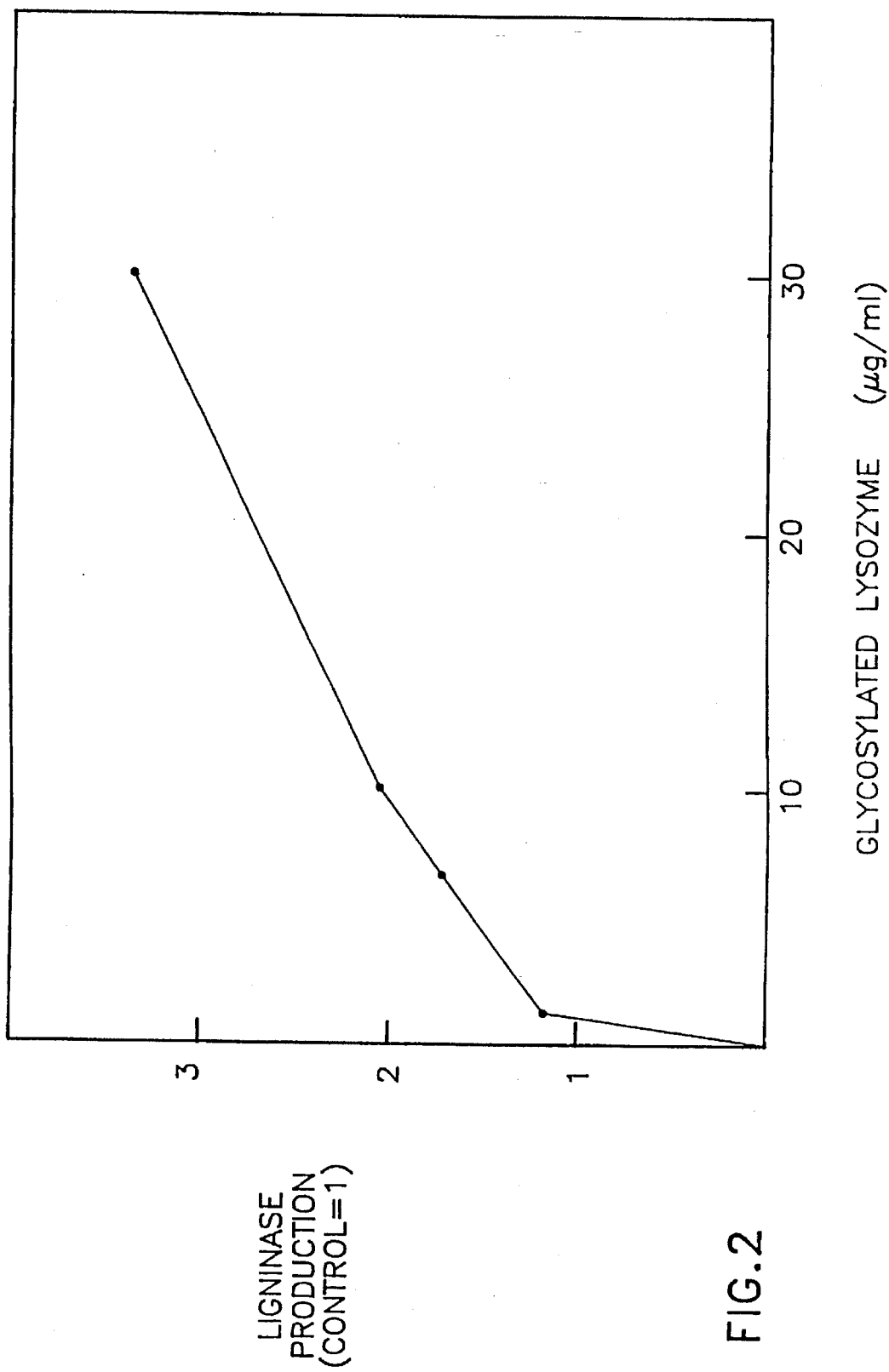
FIG. 2 shows the variation of the amount of useful metabolite produced with elicitor concentration, in accordance with another embodiment of the method of the invention.
Figure 3:
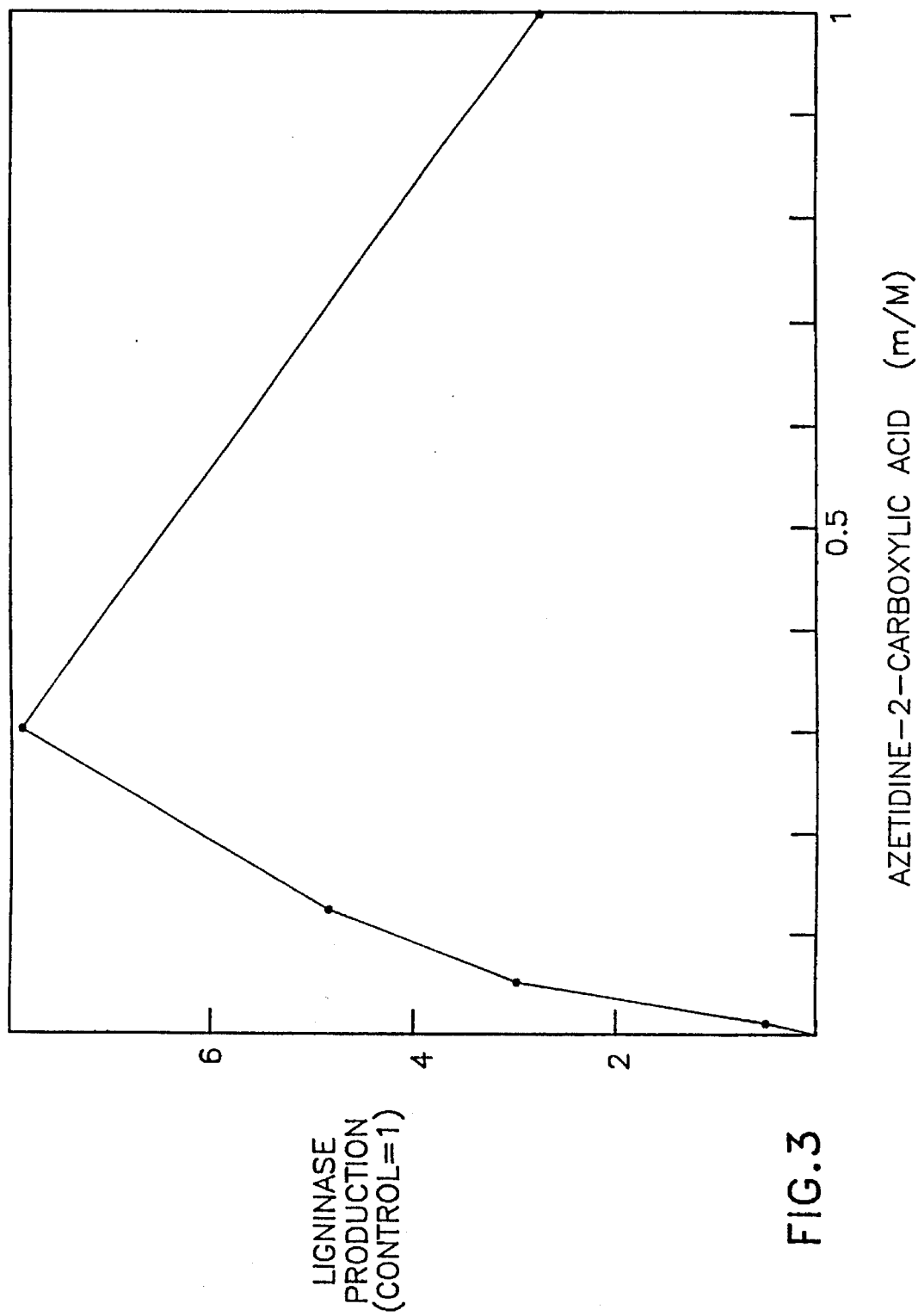
FIG. 3 shows the variation of the amount of useful metabolite produced with elicitor concentration, in accordance with a further embodiment of the method of the invention.

FIG. 1 shows the variation of the amount of ligninase produced with oxidized BSA concentration, in similar experiments to the foregoing. FIG. 2 shows the variation of the amount of ligninase produced with the concentration of glycosylated lysozyme (instead of oxidized BSA), in otherwise similar experiments to the foregoing; in this connection, we have found that the use of unmodified lysozyme has a negative effect, reducing the yield of ligninase to one-third of the control. FIG. 3 shows the variation of the amount of ligninase produced with the concentration of azetidine-2-carboxylic acid, which acts on the fungus cells to produce modified protein in situ (instead of oxidized BSA), in otherwise similar experiments to the foregoing.

PREPARATION OF ELICITORS

Preparation A; Conversion to Thioether Moieties in Proteins and Polypeptides to Sulfoxide Bovine serum albumin fraction V, lysozyme, hemoglobin, collagen and poly-L-methionine (MW in the range of $16-36 \times 10^3$) were each (separately) oxidized in 0.25N HCl with 0.3M hydrogen peroxide at 23° C. for one hour. The mixture was then dialyzed and lyophilized. The sulfoxide content of the product was demonstrated by reduction to thioether with 0.8M 2-mercaptoethanol for 48 min. at 37° C., the sulfone moieties not being reducible under these conditions. Analysis showed that 80–90% of the thioether moieties of the protein methionine residues had been converted to sulfoxide.

Preparation B: Glycosylation of Proteins
Introduction

Irreversible glycosylation of proteins occurs progressively in a protein-glucose mixture, with elimination of the elements of water. This process leads to a rearrangement of the nonenzymatic addition product of glucose with protein amino groups, the Amadori product. Proteins modified by advanced glycosylation continue to accumulate, and in tissue proteins serve as biological markers of protein age (Monnier et al, P.N.A.S. 1984, 81: 583).

Method

Protein (either lysozyme or protamine: 1 g.) and glucose (300 mg.) were dissolved in water (100 ml.), and the mixture adjusted to pH 8.5 with ethanolamine and lyophilized. The residue was transferred to a humidity chamber at 50° C. with saturated KI (1 g. KI in 0.5 ml. water at 100° C. to ensure supersaturation at 50° C.) to obtain 65% relative humidity. The protein-glucose mixture was kept in the humidity chamber for at least one week (after 3 days, 25–30% glycosylation; after 7 days, about 50% glycosylation). Thereafter, the protein-glucose mixture was dissolved in 100 ml. water, dialyzed against water and finally lyophilized.

In place of the exemplary lysozyme or protamine there may be used one of the sulfoxide-containing products of Preparations A or C (below).

Preparation C: Isolation of Native Proteins from Legumes

Proteins were extracted from dry seeds of pea cv. Progress No. 9. The seeds were crushed, milled and extracted with phosphate buffer (0.2M, pH 6.0). The proteins were precipitated from the extract with 10% (v/v) aqueous trichloroacetic acid solution. After centrifuging, the precipitate was dissolved in water, dialyzed and lyophilized. The amino acid analysis of these proteins, after basic hydrolysis, indicated that 20% of their methionine residues were present as the corresponding sulfoxide.

While certain embodiments of the invention have been particularly described, it will be appreciated by persons skilled in the art that many variations and modifications may be made without departing from the scope and spirit of the invention. These embodiments are therefore to be construed merely illustratively, and the scope of the invention is to be regarded as defined rather by the claims which follow:

We claim:

1. A method for culturing cells to produce a metabolite comprising growing cells selected from the group consisting of plant and fungi cells in a culture medium containing an elicitor to increase production of said metabolite, said elicitor being selected from the group consisting of oxidized BSA, glycosylated BSA, oxidized lysozyme, glycosylated lysozyme and azetidine-2-carboxylic acid, and being in an amount effective to increase production of said metabolite in an amount of at least 1000% over the production of said metabolite by said method when said elicitor is not present in said culture medium, and recovering said metabolite.

2. The method of claim 1 wherein said metabolite production is increased in an amount of at least 10,000 percent over the production of said metabolite by said method when said elicitor is not present in said culture medium.

3. The method of claim 1 wherein carborundum particles are present in said cell culture medium in an amount effective to abrade the cells to improve contact between the cells and said elicitor.

4. The method of claim 1 wherein a vanadium compound is present in said culture medium to neutralize one or more proteases produced by said cells which act to counteract the presence of said elicitor.

5. The method of claim 1 wherein said elicitor selected is oxidized BSA.

6. The method of claim 1 wherein said elicitor selected is oxidized lysozyme.

7. The method of claim 1 wherein said elicitor selected is glycosylated BSA.

8. The method of claim 1 wherein said elicitor selected is glycosylated lysozyme.

9. The method of claim 1 wherein said elicitor is azetidine-2-carboxylic acid.

10. The method of claim 1 wherein said cells are plant cells.

11. The method of claim 10 wherein said metabolite production is increased in an amount of at least 10,000 percent over the production of said metabolite by said method when said elicitor is not present in said culture medium.

12. The method of claim 10 wherein carborundum particles are present in said cell culture medium in an amount effective to abrade the cells to improve contact between the cells and said elicitor.

13. The method of claim 10 wherein a vanadium compound is present in said culture medium to neutralize one or more proteases produced by said cells which act to counteract the presence of said elicitors.

14. The method of claim 10 wherein said elicitor selected is oxidized BSA.

15. The method of claim 10 wherein said elicitor selected is oxidized lysozyme.

16. The method of claim 10 wherein said elicitor selected is glycosylated BSA.

17. The method of claim 10 wherein said elicitor selected is glycosylated lysozyme.

18. The method of claim 10 wherein said elicitor is azetidine-2-carboxylic acid.

19. The method of claim 1 wherein said metabolite is nicotine and said cells are tobacco plant cells.

20. The method of claim 2 wherein said metabolite it nicotine and said cells are tobacco plant cells.

21. The method of claim 1 wherein said metabolite is nicotine and said elicitor is oxidized BSA.

22. The method of claim 1 wherein said metabolite is atropine and said cells are *Belladonna atropa* cells.

23. The method of claim 2 wherein said metabolite is atropine and said cells are *Belladonna atropa* cells.

24. The method of claim 1 wherein said metabolite is atropine and said elicitor is oxidized BSA.

25. The method of claim 1 wherein said metabolite is diosgenin and said cells are *Dioscorea deltoides* cells.

26. The method of claim 2 wherein said metabolite is diosgenin and said cells are *Dioscorea deltoides* cells.

27. The method of claim 1 wherein said metabolite is diosgenin and said elicitor is oxidized BSA.

28. The method of claim 1 wherein said metabolite is one or more alkaloids selected from the group consisting of vinblastine, vincristine, catharantine and ajmalicine and said cells are *Catharanthus roseus* cells.

29. The method of claim 25 wherein said metabolites are produced in an increased amount of at least about 10,000 percent.

30. The method of claim 28 wherein said elicitor is oxidized BSA.

31. The method of claim 1 wherein said cells are fungi cells.

32. The method of claim 31 wherein carborundum particles are present in said cell culture medium in an amount effective to abrade the cells to improve contact between the cells and said elicitor.

33. The method of claim 31 wherein a vanadium compound is present in said culture medium to neutralize one or more proteases produced by said cells which act to counteract the presence of said elicitors.

34. The method of claim 31 wherein said metabolite is ligninase and said cells are white rot fungus cells.

35. The method of claim 34 wherein said metabolite is ligninase and said elicitor is oxidized BSA.

36. The method of claim 34 wherein said metabolite is ligninase and said elicitor is glycosylated BSA or glycosylated lysozyme.

37. The method of claim 34 wherein said metabolite is ligninase and said elicitor is azetidine-2-carboxylic acid.

* * * * *

UNITED STATES PATENT AND TRADEMARK OFFICE
CERTIFICATE OF CORRECTION

PATENT NO. : 5,552,307

DATED : September 3, 1996

INVENTOR(S) : Bezalel Kessler, et al.

It is certified that error appears in the above-identified patent and that said Letters Patent is hereby corrected as shown below:

Title page, item [75], delete "Rehobot" and insert --Rehovot--; and

Col. 2, line 6, delete "request" and insert --respect--.

Signed and Sealed this

Eighteenth Day of November 1997

Attest:

BRUCE LEHMAN

Attesting Officer

Commissioner of Patents and Trademarks